(12) United States Patent
Smith et al.

(10) Patent No.: US 6,918,910 B2
(45) Date of Patent: Jul. 19, 2005

(54) IMPLANTABLE DISTRACTION DEVICE (76) Inventors: John T. Smith, 1291 E. 3rd Ave., Salt Lake City, UT (US) 84103; Sohrab Gollogly, 1291 E. 3rd Ave., Salt Lake City, UT (US) 84103; Robert A. Van Wyk, 10801 Starkey Rd., No. 104-16, Largo, FL (US) 33777

( * ) Notice: Subject to any disclaimer, the term of this patent is extended or adjusted under 35 U.S.C. 154(b) by 0 days.

(21) Appl. No.: 10/737,534

(22) Filed: Dec. 15, 2003

(65) Prior Publication Data
US 2004/0153067 A1 Aug. 5, 2004

Related U.S. Application Data (60) Provisional application No. 60/433,563, filed on Dec. 16, 2002.

(51) Int. Cl.7 ............................................. A61B 17/68
(52) U.S. Cl. ............................. 606/60; 606/57; 606/63
(58) Field of Search .......................... 606/53, 57, 58, 606/60, 63, 90, 105

(56) References Cited

U.S. PATENT DOCUMENTS

| | | | |
|---|---|---|---|
| 5,356,411 A | * | 10/1994 | Spievack ................... 606/63 |
| 5,536,269 A | | 7/1996 | Spievack |
| 5,702,389 A | | 12/1997 | Taylor et al. |
| 6,036,690 A | * | 3/2000 | De La Plaza Fernandez . 606/53 |
| 6,106,525 A | * | 8/2000 | Sachse ........................ 606/59 |
| 6,277,124 B1 | | 8/2001 | Haag |
| 6,514,255 B1 | | 2/2003 | Ferree |
| 6,565,576 B1 | * | 5/2003 | Stauch et al. ............... 606/105 |
| 6,673,079 B1 | * | 1/2004 | Kane ........................... 606/105 |

FOREIGN PATENT DOCUMENTS

CA 2051665 9/2000

OTHER PUBLICATIONS www.asaminorthamerica.org/main/archive/1997jan.html (Taylor Spatial Frame Disorients Llizarovians).

* cited by examiner

Primary Examiner—David O. Reip
(74) Attorney, Agent, or Firm—Thorpe North & Western LLP (57) ABSTRACT

A subcutaneously implantable distraction device comprises a first arm, having a first skeletal connector for attachment to a first skeletal component at a first location. A second arm has a second skeletal connector for attachment to a second skeletal component at a second location. The first and second arms are slidably moveable with respect to each other. A fluid actuator is associated with each of the first and second arms to apply a separating force between the arms to slidably move at least one of the arms relative to the other.

18 Claims, 9 Drawing Sheets

IMPLANTABLE DISTRACTION DEVICE

The application claims priority of U.S. Provisional Patent Application No. 60/433,563, filed Dec. 16, 2002, which is herein incorporated by reference.

BACKGROUND OF THE INVENTION

1. Field of the Invention

The present invention relates generally to distraction devices for use in medical procedures. More particularly, the present invention relates to subcutaneously implantable distraction devices.

2. Related Art

The need to apply distraction, or separation, forces is often required in a variety of medical procedures. For example, treatment of conditions such as congenital deformities, limb length inequalities, traumatic bone defects, and mal-alignments of the skeleton often require that bones or bone structure be moved to, and/or held by force in, a particular position for a particular duration of time. Many conventional distraction devices are primarily external devices, that is, much of the structure includes fixators and frames disposed outside of a patient's body. Examples of such external devices include the Ilizarov fixator and the Taylor Spatial Frame.

While such external devices have been used with some degree of success, they have proved problematic in a number of areas. For example, such external devices generally require percutaneous hardware that connects the external components of the devices with the internal components of the patient's skeletal structure. The presence of hardware running through the skin can lead to higher incidents of infection. Also, externally exposed hardware is susceptible to impact during ordinary activity, which can damage the hardware and/or compromise the hardware installation.

In addition to these known external devices, some distraction devices have been developed which incorporate internal fixation hardware. That is, such devices are at least partially implantable beneath a patient's skin. One such example is sold under the mark Titanium Rib® by the Synthes Corporation and was developed by Robert Campbell. This technology is the subject of Canadian Patent No. 2,051,665 and is often used to treat Thoracic Insufficiency Syndrome.

The Campbell device is generally comprised of two overlapping metal slats which attach at opposing ends to two rib elements. To install the device, an incision is made in a patient and the two slats are generally individually attached at opposing ends to two spatially distant rib elements. The ribs are distracted by forcibly extending the two slats to a desired length, at which point the length of the device is fixed by attachment of a complex latch mechanism to each slat. The incision is then generally closed. When it is desired to distract the two ribs to a greater extent, the patient is "opened" again and the latch mechanism is removed from the two slats. The two slats are then again forcibly extended and latched in position.

While such internal devices have proved successful in some applications, they have typically proved problematic in that the devices must be surgically exposed by incising the patient's skin each time an adjustment is made. Once exposed, the devices must be manually adjusted to a desired length. Finally, once the adjustment procedure is complete, the incision must be closed and allowed to heal. Accordingly, the adjustment procedure for such devices has proved overly complicated and prone to the problems inherent in general surgical procedures. In addition, such devices are generally limited in the available range of distraction, as the devices have a maximum extension length, that, once reached, requires that the device be completely removed and replaced with a similar device with a greater extension length.

SUMMARY OF THE INVENTION

It has been recognized that it would be advantageous to develop an implantable distraction device that can be extended using only minor surgical procedures and application of external forces of a relatively small magnitude. It has also been recognized that it would be advantageous to develop an implantable distraction device that can be reconfigured after implantation to have a greater overall distraction length.

The invention provides a subcutaneously implantable distraction device that can include a first arm having a first skeletal connector configured to be attached to a first skeletal component at a first location. A second arm can have a second skeletal connector for attachment to a second skeletal component at a second location. The first and second arms can be slidably moveable with respect to each other. A fluid actuator can be associated with the first and second arms to apply a separating force between the arms to slidably move at least one of the arms relative to the other.

In accordance with another aspect of the invention, an implantable distraction device is provided that can include a first arm having a first skeletal connecter for attachment to a first skeletal component at a first location. A second arm can have a second skeletal connector for attachment to a second skeletal component at a second location. Actuating means can be disposed between the first and second arms for moving at least one of the first and second arms relative to the other. Restraining means can be operatively disposed between the first and second arms for maintaining the first and second arms in a distracted configuration.

In accordance with another aspect of the invention, an implantable distraction device is provided that can include a first arm including an outer casing and a first skeletal connector for coupling to a first skeletal component at a first location. A second arm can include an inner piston and a second skeletal connector for coupling to a second skeletal component at a second location. The inner piston can be at least partially disposed within the outer casing. A fluid cavity can be defined between the outer casing and the inner piston. Fluid delivery means can be operatively coupled to the fluid cavity, for delivering pressurized fluid to the fluid cavity to cause the first and second arms to slidably move in a separating direction.

In accordance with another aspect of the invention, a method of distracting a first skeletal component and a second skeletal component relative to each other is provided and includes the steps of: coupling a first arm to the first skeletal component; coupling a second arm to the second skeletal component; and providing a fluid-actuated force between the first and second arms to slidably move at least one of the first and second arms relative to the other to distract the first and second skeletal components relative to each other.

In accordance with another aspect of the invention, a method of distracting a first skeletal component and a second skeletal component of a patient relative to each other is provided and includes the steps of: subcutaneously implanting a first arm on the first skeletal component;

subcutaneously implanting a second arm on the second skeletal component, said second arm being operatively coupled to the first arm; subcutaneously implanting a fluid delivery conduit having an inlet port coupled thereto, said fluid delivery conduit being in operable communication with the each of the first and second arms; and percutaneously injecting a fluid through the inlet port to the fluid delivery conduit to thereby provide a fluid-actuated separation force between the first and second arms to distract the first and second skeletal components.

Additional features and advantages of the invention will be apparent from the detailed description which follows, taken in conjunction with the accompanying drawings, which together illustrate, by way of example, features of the invention.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention relates generally to subcutaneously implantable distraction devices, one example of which is shown generally in perspective, top, front and end view in FIGS. 1, 1A, 1B and 1C, respectively. The distraction device, or distractor, can be utilized in a variety of medical applications and procedures, including treatment of congenital deformities, limb length inequalities, traumatic bone defects, mal-alignments of the skeleton, thoracic insufficiency syndrome, etc. A wide range of medical applications can benefit from the present invention, particularly those applications that require incremental distraction of bones or skeletal components.

As used herein, the term "distraction" is to be understood to refer to a procedure in which two or more elements are moved a distance from each other and/or are maintained at a distance from each other. Similarly, a distraction device is a device which moves two or more elements some distance from each other and/or which maintains two or more elements at a distance from each other. The distractor of the present invention is generally used to distract skeletal components. As used herein, the term "skeletal component" is to be understood to refer to a bone or skeletal component to which the distractor may be attached or coupled. When two skeletal components are referenced, it is to be understood that the skeletal components may be two distinct bones, or may be two components of a single bone which may be fractured.

Figure 1:
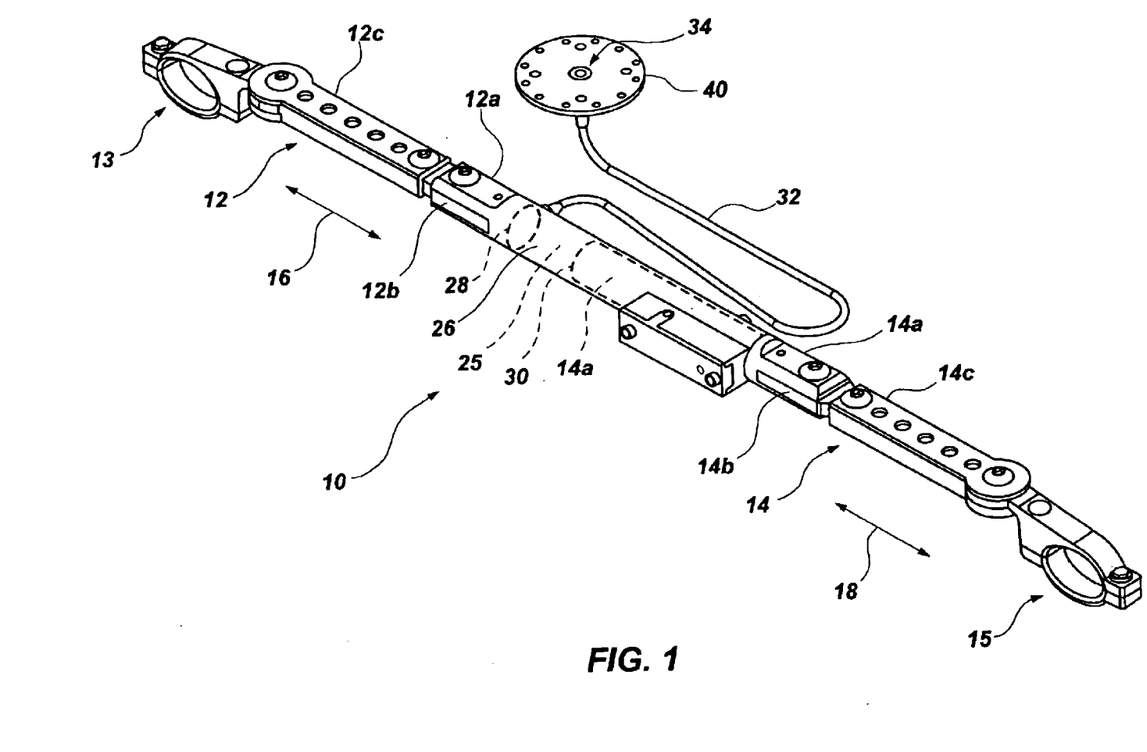
FIG. 1 is a perspective view of a distraction device in accordance with an embodiment of the present invention.
Figure 1A:
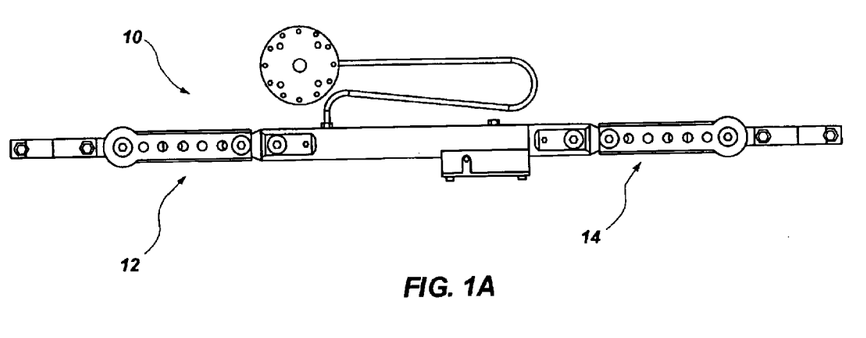
FIG. 1A is a top view of the distraction device of FIG. 1.
Figure 1B:
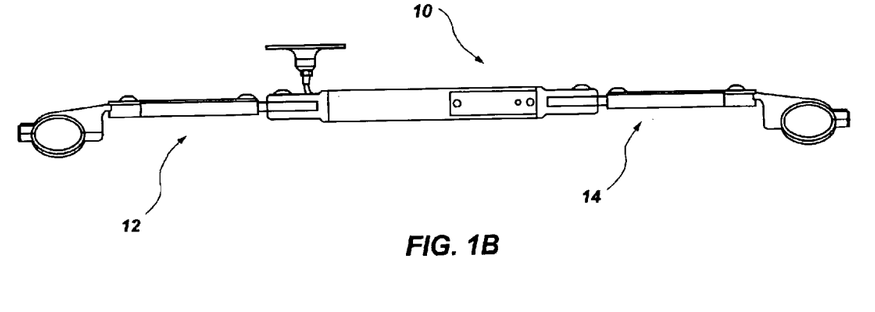
FIG. 1B is a front view of the distraction device of FIG. 1.
Figure 1C:
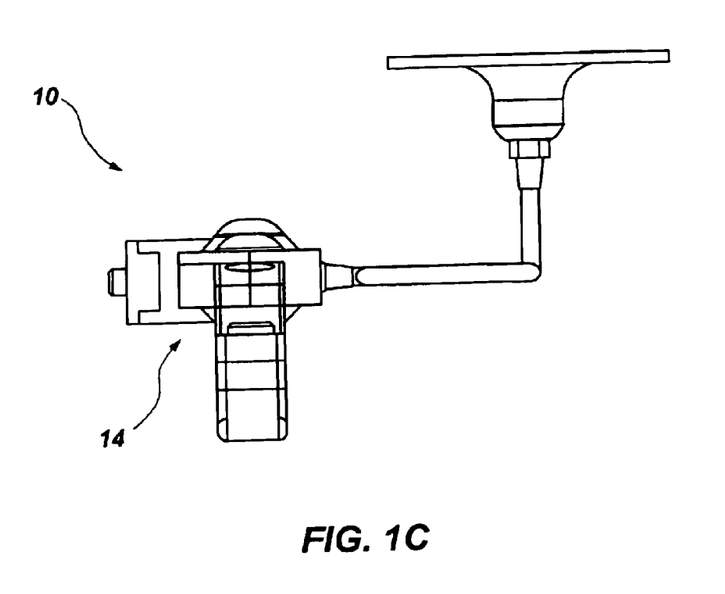
FIG. 1C is an end view of the distraction device of FIG. 1.

The distractor of FIG. 1 is shown in a retracted position and includes a first arm 12 which can have a first skeletal connector 13 attached or disposed thereon. The first skeletal connector 13 can be configured to be attached to a first skeletal component (not shown in the figures) at a first location. A second arm 14 can have a second skeletal connector 15 that is configured to be attached to a second skeletal component (not shown) at a second location. The first 12 and second 14 arms can be slidably moveable with respect to each other. Thus, arm 12 is slidably moveable as shown by arrow 16 and arm 14 is slidably movable as shown by arrow 18. The distractor can include a fluid actuator 26 which can be associated with each of the first and second arms. The actuator can be configured to apply a separating force between the arms to slidably move at least one of the arms relative to the other.

In operation, surgery is initially performed in which skeletal components of a patient are exposed by forming an incision over the area in which the distractor will be implanted. Each of the skeletal connectors 13, 15 can then be connected, coupled or attached to an individual exposed skeletal component. During installation or attachment of the distractor, an initial length of the distractor can be established, as discussed in more detail below. Once the distractor is properly attached and positioned, the incision can be closed, with each of the components of the distractor remaining beneath the patient's skin. When it is desired to distract the skeletal components, the fluid actuator 26 can be activated to force the arms 12, 14 to slidably move in a separating direction. When the desired distraction is reached, the distractor can maintain or restrain the distracted position in a variety of ways, as discussed in further detail below. Activation of the distractor can be advantageously accomplished with little or only minor surgery being required.

While the arms are indicated generally by reference numbers 12 and 14, the arms can be comprised of one or more separate segments which collectively form the arm, as illustrated for example by the various segments 12a, 12b and 12c of arm 12. In the embodiment shown in FIG. 1, the distractor includes two central arm segments, 12a and 14a (also shown in exploded view in FIG. 2). In this aspect, arm segment 12a includes a generally cylindrical hollow sleeve in which arm segment 14a is disposed. Thus, the arms in this embodiment are collinear, and each can move slidably with respect to the other to achieve distraction of the skeletal connectors 13, 15 and, accordingly, the skeletal components to which the connectors are attached.

While the arms shown in the figures generally include cylindrical arm components which are collinear, it is to be understood that arms of a variety of cross sections and shapes can be used. In addition, the arms may be disposed in relation to each in a variety of manners, i.e., they may lie parallel to one another and may overlap one another in a variety of manners. As discussed, the arms are generally slidable with respect to each other and can move relative to each other in a separating or a retracting direction. As used herein, the term "separating motion" is to be understood to refer to the condition when the arms are moving relative to each other such that opposing ends of the arms (i.e., the ends with which the skeletal connectors are associated) are growing further apart. Similarly, the term "separating force" is to be understood to refer to a force that tends to move the arms in a separating motion.

The arms of the present invention are generally distracted with an actuator or actuating means. The actuator can be a variety of those known in the art, including mechanical, electrical, fluid, etc. In some aspects of the invention, a fluid actuator is utilized to distract the arms. The fluid actuator of the present invention can be of a variety of fluid actuators known in the art such as a hydraulic actuator or a pneumatic actuator. In the embodiment illustrated in FIG. 1, the fluid actuator is formed by arm segment 12a that includes a cylinder, and by arm segment 14a that includes a rod section disposed within the cylinder of arm segment 12a. In this aspect, the arm segments 12a and 14a collectively define a cavity, shown by example at 25, formed between an inside end 28 of the cylinder of arm 12a and an inside end 30 of the rod of arm 14a. The cavity 25 can be provided with fluid flow which will result in the ends 28, 30 moving away from each other.

The fluid actuator of the present invention can be provided with fluid flow in a variety of ways. In the embodiment illustrated in FIG. 1, a fluid delivery conduit 32 is operatively coupled to the actuator, i.e., to the cavity 25 between the arms 12a and 14a. The fluid delivery conduit can include terminal cap 40 having an inlet port 34 formed therein. Fluid flow can be provided through the inlet port 34 to pressurize the cavity 25 to create a separating force to cause the arms to move relative to each other. Fluid can be delivered to the fluid delivery conduit in a number of ways, and in one aspect of the invention the fluid is delivered through the inlet port 34 by a syringe (not shown). In this aspect of the invention, a syringe is inserted or threaded into the inlet port and a fluid contained in the syringe can be forced out of the syringe, through the fluid delivery conduit 32 and into fluid cavity 25. The fluid flow results in the cavity becoming pressurized, which in turn results in the arms 12a and 14a moving outwardly from each other.

The fluid used in the fluid actuator can be of a variety of types, including a hydraulic fluid when the actuator is hydraulically actuated, or a gas fluid when the actuator is pneumatically actuated. In one aspect of the invention, a hydraulic actuator is used and saline solution is used as the hydraulic fluid. By advantageously using saline solution, leakage of the hydraulic fluid becomes less of a concern, as saline solution is generally bio-compatible. Thus, the hydraulic actuator can be more simply designed and built as leakage concerns are not a primary consideration. In addition, in the case where it may be undesirable to maintain pressure in the actuator once distraction is complete, the hydraulic actuator can simply be drained into surrounding tissue without producing adverse health effects.

Figure 3:
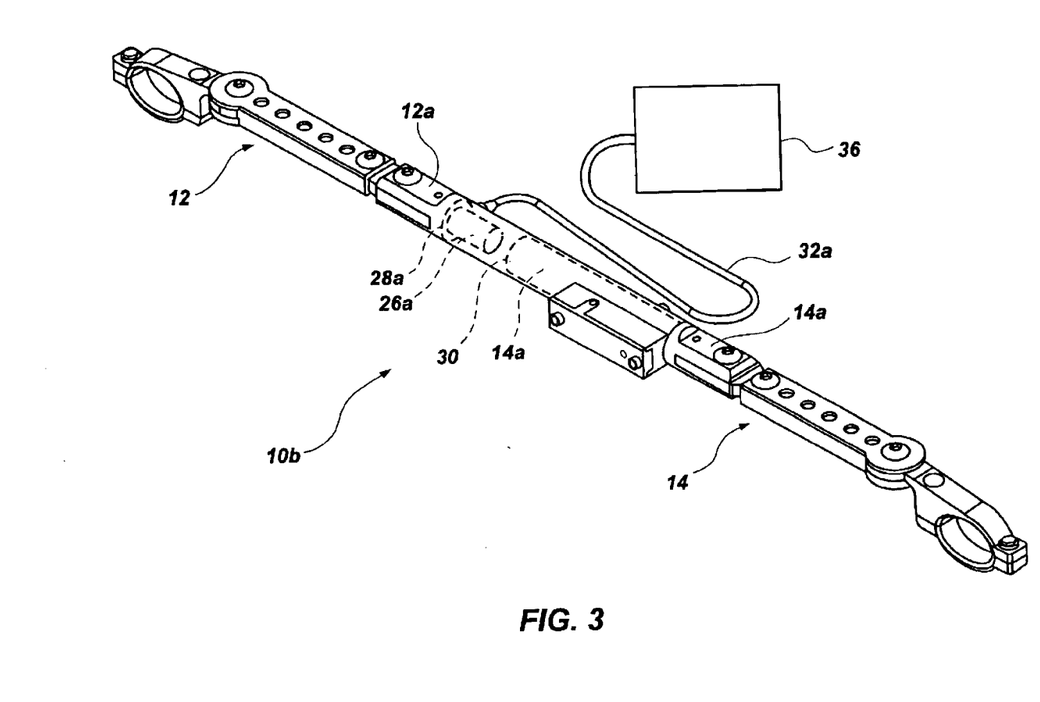
FIG. 3 is a perspective view of another distraction device in accordance with an aspect of the invention.

While the embodiment illustrated in FIG. 1 includes a fluid actuator formed of or defined by the distractor arms, in other aspects of the invention a conventional hydraulic actuator can be coupled to the arm segments to apply force to the arms. As shown in FIG. 3, the distractor 10b can include a stand-alone fluid actuator 26a disposed between an inside end 28 of arm segment 12a and an inside end 30 of arm segment 14a. In this aspect, fluid delivery conduit 32a can deliver pressurized fluid to the actuator 26a which results in the actuator applying a separating force to the arms at arm ends 28 and 30. The fluid can be pressurized by a pump (shown schematically for exemplary purposes at 36). It will be appreciated that each of the actuator 26a and pump 36 can be of a variety of types known to those in the art, and each can be disposed in a variety of positions relative to the distractor. For example, the actuator 26a can be disposed outside of the arms of the distractor.

Figure 4A:
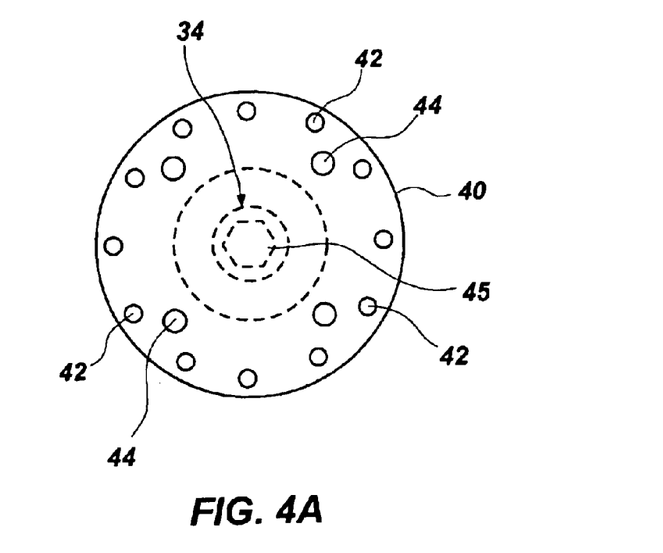
FIG. 4A is a top view of a cap of a fluid delivery conduit in accordance with one embodiment of the invention.
Figure 4B:
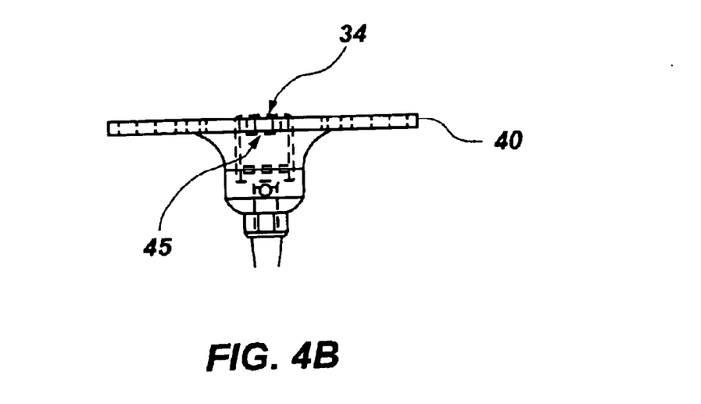
FIG. 4B is a front view of the cap of FIG. 6A.

As shown in more detail in FIGS. 4A and 4B, terminal cap 40 can include a variety of advantageous features. In one aspect of the invention, the terminal cap, and accordingly, the inlet port 34, can be subcutaneously implanted in a patient. In this embodiment, the distractor, the fluid conduit and the inlet port are each implanted in the patient to facilitate adjustment of the distractor with little or no surgery required. The cap 40, which can be disposed directly below a patient's skin, can include one or more perimeter perforations 42 which can be used to suture the cap beneath the patient's skin. Engagement perforations 44 can be formed in the cap to enable tooling or other equipment to grasp the cap without comprising the suture structure.

A plug 45 can be disposed in the inlet port 34 to prevent unwanted material from entering the port, and thus the delivery conduit 32 and/or the distractor. The plug 45 can be threadably engaged in the inlet port to hold the plug more securely. In this case, as some force may be required to threadably disengage the plug, tooling or other equipment can engage perforations 44 to secure the cap 40 while the plug is being removed. In this embodiment, the threads in the inlet port which hold the plug can also be used to threadably engage a syringe into the inlet port when applying fluid through the port.

In the aspect discussed above, an incision will generally be made in the skin immediately over the plug 45 to create access to the plug. However, in addition to utilizing a threaded, removable plug, a substantially pliant, non-removable plug can be utilized. In this aspect of the invention, the substantially pliant plug can be pierced with a needle of a syringe to enable fluid flow to be delivered through the needle into the delivery conduit without requiring removal of the plug. In this aspect of the invention, an incision may not be necessary, as the needle can simply pierce the patient's skin prior to entering the plug and injecting the fluid.

Figure 2:
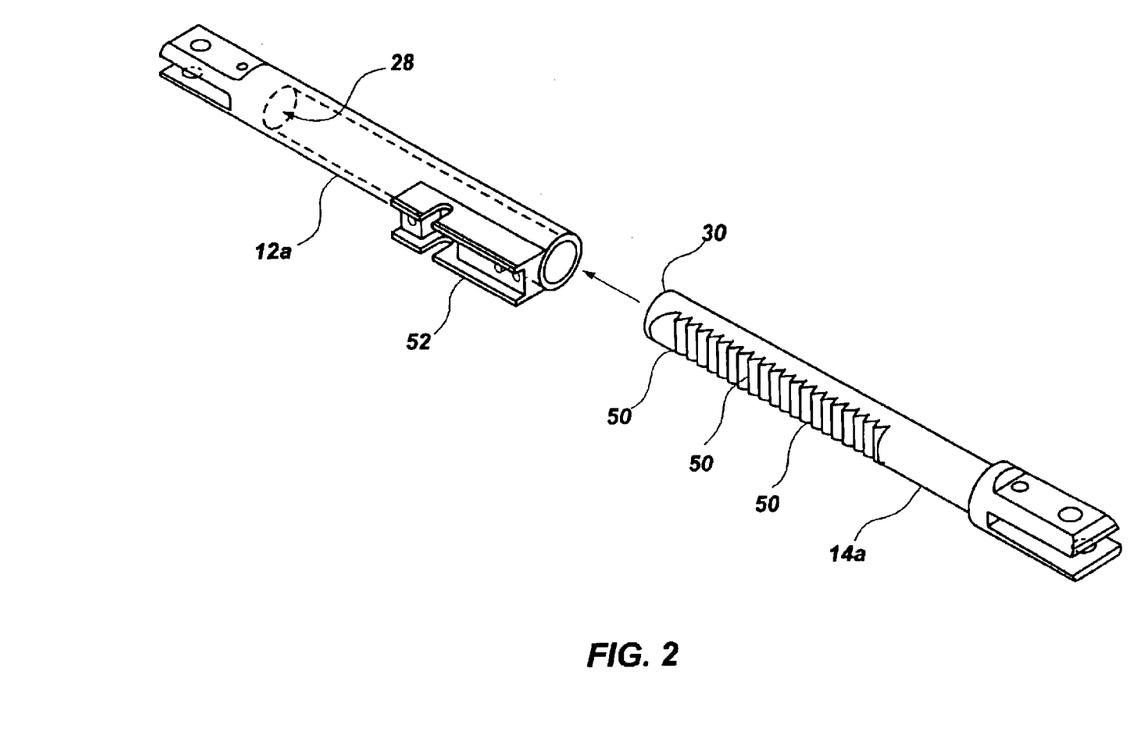
FIG. 2 is an exploded perspective view of two central arm segments of the distraction device of FIG. 1.

The present invention can include restraining means for maintaining of restraining the distractor arms in a distracted position. As shown in FIG. 2, arm segment 14a can include a series of notches or teeth 50 which can be used to restrain or maintain separation of the arms as the arms are incrementally moved apart. Arm segment 12a can include a housing 52 in which a restraining assembly can be disposed to engage the teeth 50 of arm segment 14a. As shown assembled in FIG. 5, the restraining or maintaining assembly can include an anchoring element 53 which can be coupled within the housing 52. A rocker element 54 can be rotatably coupled within the housing 52. A biasing element 56, which can be, for example, similar to a leaf spring, can be coupled to the anchoring element 53. As will be appreciated from study of FIG. 5, once the restraining or maintaining assembly is in place, rocker 54 is prevented from rocking counter-clockwise by anchoring element 53. Biasing element 56 applies a biasing force that serves to return the rocker into contact with the anchoring element if the rocker is displaced with force sufficient to overcome the biasing force. For additional clarity, the anchoring, rocking and biasing elements are each shown in perspective view in FIGS. 5A, 5B and 5C, respectively.

Figure 5:
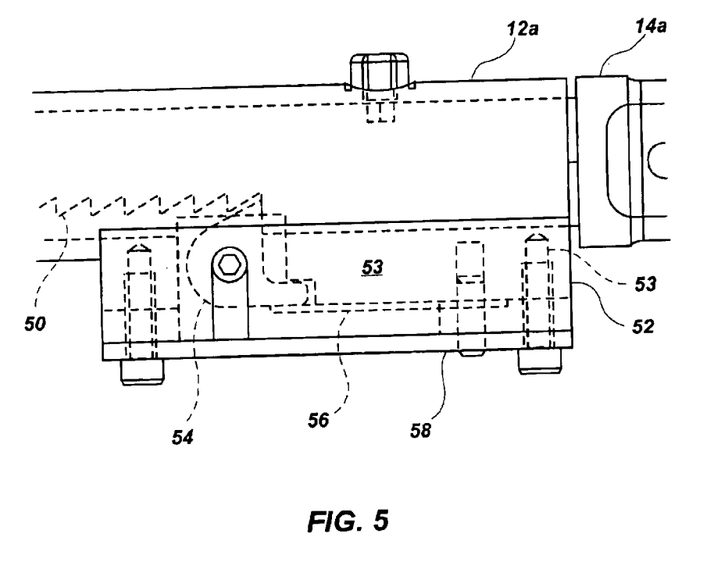
FIG. 5 is a partial top view of one embodiment of a restraining assembly in accordance with one aspect of the invention.
Figure 5A:
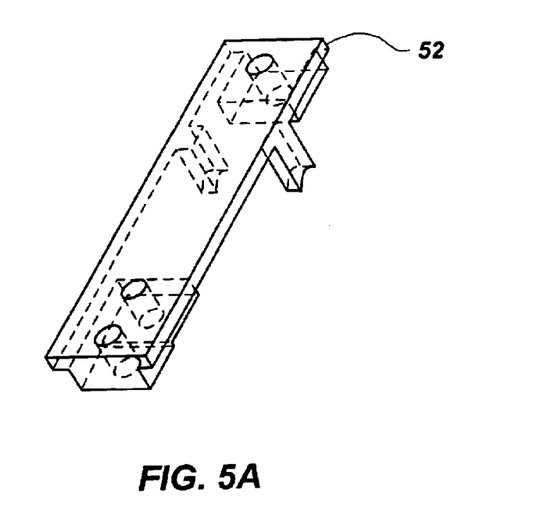
FIG. 5A is a perspective view of an anchoring component of the restraining assembly of FIG. 5.
Figure 5B:
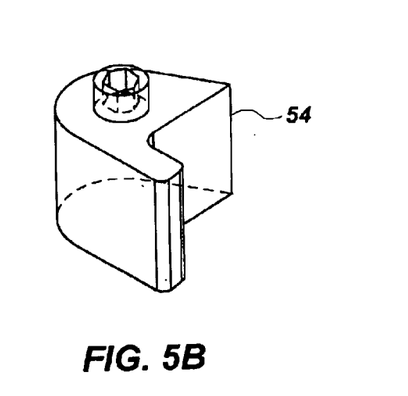
FIG. 5B is a perspective view of a rocker component of the restraining assembly of FIG. 5.
Figure 5C:
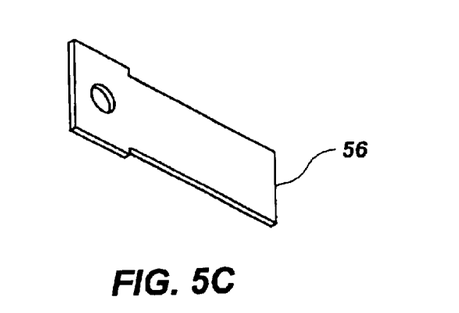
FIG. 5C is a perspective view of a biasing component of the restraining assembly of FIG. 5.

Thus, as the teeth 50 of arm segment 14a move to the right of the page of FIG. 5, the rocker is rotated clockwise until the tooth in contact with the rocker passes by the rocker. At this point, the rocker is returned to an upright position by the biasing element, where it prevented from rotating further in a counter-clockwise direction by the anchoring member 53. Thus, in the case where the arm segment 14a is subjected to forces tending to contract the distractor, the rocker 54 prevents the tooth in immediate contact with it from moving further to the left of the page of FIG. 5. This feature is advantageous in that the fluid actuator need not apply constant force to the distractor to maintain a distracted configuration, as the maintaining assembly provides incremental stops which prevent the distractor arms from contracting relative to each other. Thus, the restraining assembly allows movement of the arms 12, 24 in a distracting motion, but retains the arms from contracting or retracting from a distracted position.

Figure 6:
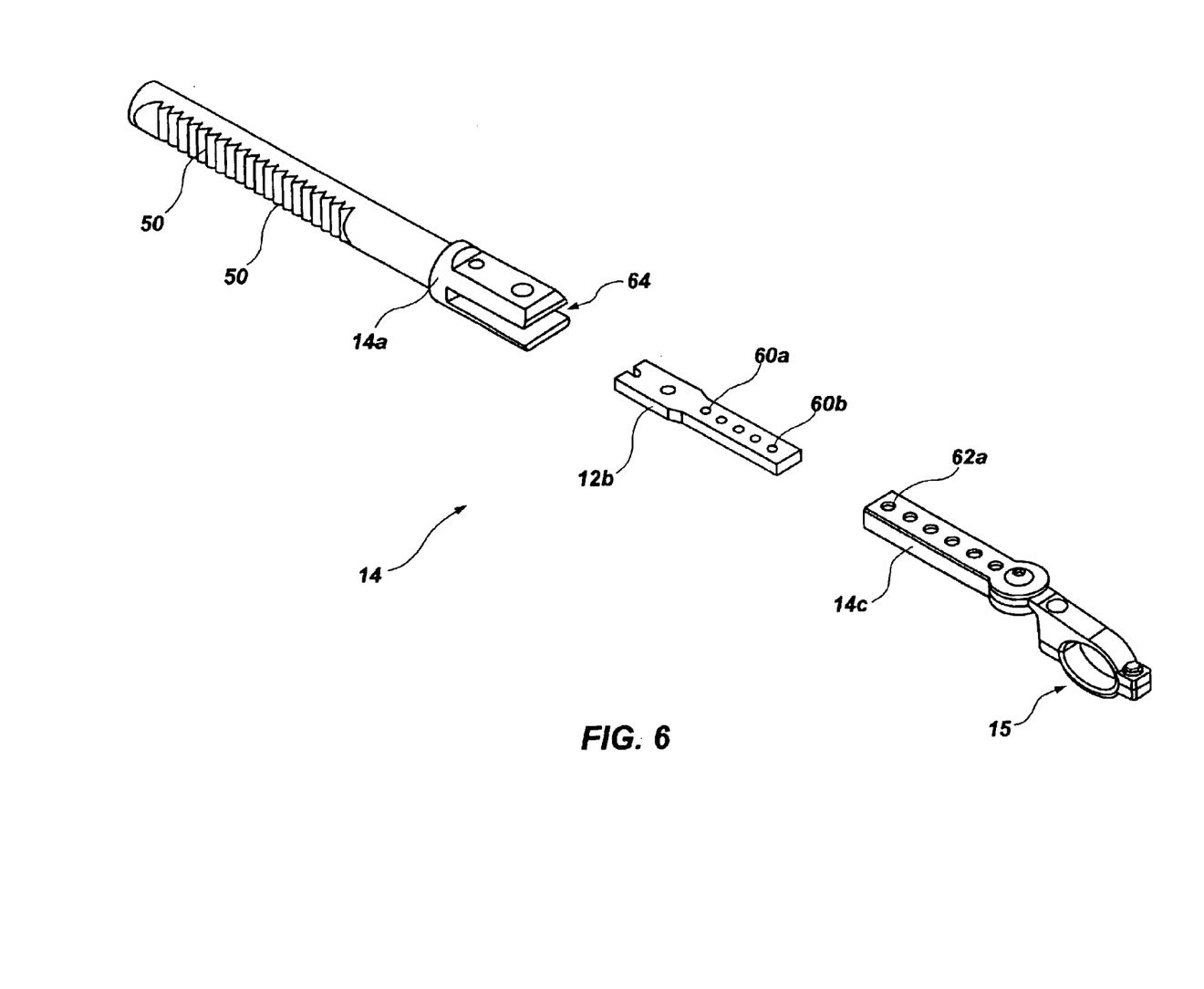
FIG. 6 is a perspective, exploded view of one embodiment of a series of arm segments of the distraction device of FIG. 1.

Shown in FIG. 6 are segments of arm 14 in an exploded configuration. This embodiment includes three arm segments, 14a, 14b and 14c. As discussed above, central arm segment 14a generally engages central arm segment 12a (not shown in FIG. 6). Intermediate arm segment 14b can engage arm segment 14a and can be fastened, for example, with bolts or screws, as would occur to one skilled in the art. Arm segment 14c then engages arm segment 14b and can similarly be bolted or screwed in place. Arm segments 14b and 14c each advantageously include an array of attachment ports 60 and 62, respectively. The attachment ports can be used to adjust an over-all length of arm 14 independently of the actuator, which controls overall length of the distractor during distraction. For example, if port 62a were aligned with port 60a, the overall length of arm 14 would be at a minimum. If port 62a were aligned with port 60b, the overall length of arm 14 would be at a maximum. By aligning and attaching various ports 62 with various ports 60, the overall length of arm 14 can be adjusted through a variety of lengths.

The adjustable length of arm 14 can be used to increase the length span over which the distractor can be used. In the case where the distractor has reached the maximum extension possible, i.e., where arm segment 14a is physically limited from traveling further from arm segment 12a, the length adjustment feature of the arms can be used to obtain further extension. For example, once arm segment 14a is fully extending, the fasteners which secure segments 14a and 14b together can be removed. Segment 14b can then be laterally removed from receiving notch 64 in arm segment 14a, thus freeing arm segment 14a to be rotated within arm segment 12a (not shown in FIG. 6). In this manner, the maintaining or ratcheting assembly can be disengaged from teeth 50 and arm segment 14a can be slidably contracted further inside arm segment 12a (i.e., toward "zero" extension of arm segments 12a and 14a). Arm 14 can then be lengthened by removing the connectors coupling segments 14b and 14c and extending the overall length of the two segments, as discussed above.

It will be appreciated that the above-described adjustment can be accomplished without removing the skeletal connectors 13, 15 from their respective skeletal components. Thus, once the skeletal connectors are attached, they need not be detached to adjust the overall length of the distractor. In addition, the overall length of the distractor arms 12, 14 can be adjusted when installing the distractor, to ensure that a proper fit is made while also ensuring the distraction process begins with arm segments 12a and 14a in their most contracted position. Also, as each arm 12, 14 can include adjustable-length segments, the overall length of the distractor can be adjusted in an amount twice that provided by each arm 12, 14.

While the skeletal connectors 13, 15 are generally shown in the figures as collars, the skeletal connectors can take a variety of forms, including threaded fasteners, hooks, etc., as would occur to one skilled in the art. Similarly, while the maintaining means are shown in the figures as a ratcheting assembly, it is to be understood that the maintaining means can be of a variety of similar structures, including selectively activated clamping systems and the like.

In addition to the structural features detailed above, the present invention also provides a method of distracting a first skeletal component and a second skeletal component relative to each other. The method can include the steps of: coupling a first arm to the first skeletal component; coupling a second arm to the second skeletal component; and providing a fluid-actuated force between the first and second arms to slidably move at least one of the first and second arms relative to the other to distract the first and second skeletal components relative to each other.

The step of providing a fluid-actuated force between the first and second arms to slidably move at least one of the first and second arms relative to the other can include the further step of actuating a hydraulic actuator operatively coupled to each of the first and second arms. The method can include the further step of actuating the hydraulic actuator with saline solution. The step of providing a fluid-actuated force between the first and second arms to slidably move at least one of the first and second arms relative to the other can include the further step of actuating a hydraulic actuator defined by the first and second arms. The method can include the further step of maintaining the first and second arms in a distracted position with a maintaining assembly independent of the fluid-actuated force. A further step can include extending a length of at least one of the first and second arms with a length adjusting assembly independent of the fluid-actuated force.

In accordance with another aspect of the invention, a method of distracting a first skeletal component and a second skeletal component of a patient relative to each other is provided and includes the steps of: subcutaneously implanting a first arm on the first skeletal component; subcutaneously implanting a second arm on the second skeletal component, said second arm being operatively coupled to the first arm; subcutaneously implanting a fluid delivery conduit having an inlet port coupled thereto, said fluid delivery conduit being in operable communication with the each of the first and second extension arms; and percutaneously injecting a fluid through the inlet port to the fluid delivery conduit to thereby provide a fluid-actuated separation force between the first and second arms to distract the first and second skeletal components. The step of percutaneously injecting a fluid through the inlet port to the fluid delivery conduit can include the step of injecting saline solution through the inlet port.

It is to be understood that the above-referenced arrangements are illustrative of the application for the principles of the present invention. It will be apparent to those of ordinary skill in the art that numerous modifications can be made without departing from the principles and concepts of the invention as set forth in the claims.

What is claimed is:

1. A subcutaneously implantable distraction device, comprising:
    a first arm having a first skeletal connector configured to be attached to a first skeletal component at a first location;
    a second arm having a second skeletal connector configured to be attached to a second skeletal component at a second location;
    the first and second arms being slidably moveable with respect to each other;
    a fluid actuator, associated with the first and second arms, the actuator being capable of applying a separating force between the arms to slidably move at least one of the arms relative to the other; and
    each of the first and second arms including at least two adjustable sections, adjustably coupled to one another to enable adjustment of a length of the first and second arms.

2. The device of claim 1, further comprising restraining means, operatively coupled to the first and second arms, for selectively restraining the arms from retracting to a retracted position.

3. The device of claim 2, wherein the restraining means further allows movement of the arms in a separating motion.

4. The device of claim 1, wherein the fluid actuator is coupled to each of the first and second arms.

5. The device of claim 1, wherein:
    the first arm includes a cylinder;
    the second arm includes a rod at least partially disposed in the cylinder; and
    the cylinder and rod form at least a portion of the fluid actuator.

6. The device of claim 1, wherein the skeletal connectors are selected from the group consisting of: a collar; a threaded fastener; and a hook.

7. The device of claim 1, wherein the fluid actuator comprises a pneumatic actuator.

8. The device of claim 1, wherein the fluid actuator comprises a hydraulic actuator.

9. The device of claim 8, wherein the hydraulic actuator is actuated by saline solution.

10. The device of claim 1, further comprising a fluid delivery conduit operatively coupled to the fluid actuator, the fluid delivery conduit including an inlet port configured to receive a syringe to facilitate delivery of fluid flow from the syringe to the actuator.

11. The device of claim 10, wherein the inlet port is a subcutaneously implantable inlet port.

12. The device of claim 1, further comprising a fluid pump operatively coupled to the actuator, the fluid pump being configured to provide fluid flow to the actuator.

13. The device of claim 12, wherein the fluid pump comprises a pump selected from the group consisting of: a pneumatic pump; and a hydraulic pump.

14. A method of distracting a first skeletal component and a second skeletal component relative to each other, comprising the steps of:
    coupling a first arm to the first skeletal component;
    coupling a second arm to the second skeletal component;
    providing a fluid-actuated force between the first and second arms to slidably move at least one of the first and second arms relative to the other to distract the first and second skeletal components relative to each other; and
    extending a length of each of the first and second arms with a length adjusting assembly independent of the fluid-actuated force.

15. The method of claim 14, wherein the step of providing a fluid-actuated force between the first and second arms to slidably move at least one of the first and second arms relative to the other includes the step of actuating a hydraulic actuator operatively coupled to each of the first and second arms.

16. The method of claim 15, comprising the further step of actuating the hydraulic actuator with saline solution.

17. The method of claim 14, wherein the step of providing a fluid-actuated force between the first and second arms to slidably move at least one of the first and second arms relative to the other includes the step of actuating a hydraulic actuator defined by the first and second arms.

18. The method of claim 14, comprising the further step of maintaining the first and second arms in a distracted position with a maintaining assembly independent of the fluid-actuated force.

* * * * *